(12) United States Patent
De Rijke et al.

(10) Patent No.: US 10,239,814 B2
(45) Date of Patent: Mar. 26, 2019

(54) PROCESS FOR THE PURIFICATION OF LEVULINIC ACID

(71) Applicant: GFBIOCHEMICALS IP ASSETS B.V., Geleen (NL)

(72) Inventors: Aris De Rijke, Geleen (NL); Rudy Francois Maria Jozef Parton, Geleen (NL); Donato Santoro, Geleen (NL); Barthel Engendahl, Geleen (NL)

(73) Assignee: GFBIOCHEMICALS IP ASSETS B.V., Geleen (NL)

( * ) Notice: Subject to any disclaimer, the term of this patent is extended or adjusted under 35 U.S.C. 154(b) by 0 days.

(21) Appl. No.: 15/767,465

(22) PCT Filed: Oct. 11, 2016

(86) PCT No.: PCT/EP2016/074355
§ 371 (c)(1),
(2) Date: Apr. 11, 2018

(87) PCT Pub. No.: WO2017/064069
PCT Pub. Date: Apr. 20, 2017

(65) Prior Publication Data
US 2018/0297927 A1 Oct. 18, 2018

(30) Foreign Application Priority Data
Oct. 12, 2015 (EP) .................... 15189403

(51) Int. Cl.
C07C 51/43 (2006.01)
C07C 59/185 (2006.01)

(52) U.S. Cl.
CPC ............ C07C 51/43 (2013.01); C07C 59/185 (2013.01)

(58) Field of Classification Search
CPC ............................. C07C 51/43; C07C 59/185
See application file for complete search history.

(56) References Cited

U.S. PATENT DOCUMENTS

| | | |
|---|---|---|
| 2,029,412 A | 2/1936 | Cox et al. |
| 2,305,738 A | 12/1942 | Scheuing et al. |
| 2,349,514 A | 5/1944 | Moyer et al. |
| 2,684,982 A | 7/1954 | Dunlop |
| 2,780,588 A | 2/1957 | Dunlop |
| 4,312,700 A | 1/1982 | Helmreich et al. |
| 4,897,497 A | 1/1990 | Fitzpatrick |
| 5,608,105 A | 3/1997 | Fitzpatrick |
| 6,054,611 A | 4/2000 | Farone et al. |
| 8,507,718 B2 | 8/2013 | Mullen et al. |
| 9,073,841 B2 | 7/2015 | Mullen et al. |
| 2010/0312006 A1 | 12/2010 | Lake |
| 2012/0178967 A1* | 7/2012 | Banner .................. C07C 51/44 562/577 |
| 2014/0316161 A1 | 10/2014 | Mullen et al. |

FOREIGN PATENT DOCUMENTS

| | | |
|---|---|---|
| EP | 2374786 A1 | 10/2011 |
| WO | 2010030617 A1 | 3/2010 |
| WO | 2014087013 A1 | 6/2014 |
| WO | 2014087016 A1 | 6/2014 |

OTHER PUBLICATIONS

Nicholas P. Wynn, Separate Organics by Melt Crystallization, Chemical Engineering Progress, Mar. 1992, pp. 52-60, Canada.
P.J. Jansens, et al., Melt Crystallization, Crystallization, 2000, pp. 966-975, Academic Press.
G.F. Arkenbout, Chapter II, Technical Equipment for Crystal Layer Growth, Melt Crystalization Technology, 1995, pp. 239-293.
Xiaobin Jiang, et al., Research Progress and Model Development of Crystal Layer Growth and Impurity Distribution in Layer Melt Crystallization: A Review; Ind. Eng. Chem. Res. 2014, vol. 53, pp. 13211-13227.
Won Seok Choi, et al., Separation of Acetic Acid from Acetic Acid-Water Mixture by Crystallization, Separation Science and Technology, 2013, vol. 48, pp. 1056-1061.

* cited by examiner

*Primary Examiner* — Yevgeny Valenrod
*Assistant Examiner* — Blaine G Doletski
(74) *Attorney, Agent, or Firm* — Hudak, Shunk & Farine Co. LPA

(57) ABSTRACT

A process for the purification of levulinic acid including the following steps: a. providing a composition 1, comprising at least 75 wt. % of levulinic acid; b. cooling composition 1 to at least one temperature Tc, wherein Tc is a temperature in the range $1.23*(W1)-104.5 \leq Tc$ (° C.)$\leq 1.23*(W1)-89.5$, wherein W1 is the weight % of levulinic acid in composition 1, to obtain a cooled composition 1; c. performing melt crystallization of composition 1 including the steps of: i. bringing the cooled composition 1 into contact with levulinic acid crystal seeds, ii. allowing the levulinic acid in composition 1 to crystallize at at least one temperature Tc to obtain crystals 1 and liquid 1, and iii. draining of liquid 1; d. optionally, treating crystals 1, after draining of liquid 1, by sweating, according to the following steps: i. heating the crystals 1 at a temperature between 5 and 40° C. to obtain crystals 2 and liquid 2, and ii. draining of liquid 2; e. melting the crystals 1 or 2, after draining of liquid 1 or 2, to obtain composition 2, f. determining the levulinic acid concentration in composition 2 and, in case the levulinic acid concentration is below a predetermined value, repeating steps b, c, optionally d, and e, as many times as necessary to obtain a final composition with a predetermined levulinic acid concentration.

18 Claims, 1 Drawing Sheet

PROCESS FOR THE PURIFICATION OF LEVULINIC ACID

FIELD OF THE INVENTION

The invention is directed to a process for the purification of levulinic acid, to a melt crystallizer for the purification of levulinic acid and to a purification section in a plant for the production of levulinic acid.

BACKGROUND OF THE INVENTION

Levulinic acid, or 4-oxopentanoic acid, is an organic compound with the formula $CH_3C(O)CH_2CH_2CO_2H$. Levulinic acid is a precursor to pharmaceuticals, plasticizers, and various other additives. Also biofuels, such as methyltetrahydrofuran, gamma-valerolactone, and ethyl levulinate, can be prepared from levulinic acid.

Levulinic acid preferably is obtained as pure as possible, as this is preferred for the further use of levulinic acid for the production of pharmaceuticals, food additives and cosmetics. For these applications levulinic acid preferably has a purity of at least 95 wt. %, more preferably of at least 98 wt. %, based on the total weight of the levulinic acid. Also various chemical conversions of levulinic acid towards its derivatives suffer in selectivity and activity due to the presence of impurities in the levulinic acid.

Levulinic acid can be obtained by degradation of cellulose that is present in C6 carbohydrate-containing feedstocks, for example in agricultural waste products, waste from the paper industry or municipal waste.

In the prior art several processes for the production of levulinic acid are described.

The production of levulinic acid by acid catalyzed hydrolysis of C6 carbohydrate-containing feedstocks is described e.g. in WO2014/087016 A1 and US2010/312006. The described processes yield a biomass hydrolysate that contains next to the desired product, levulinic acid, several by-products that are derived during conversion of C6 carbohydrate-containing feedstocks by acid catalyzed hydrolysis. A process for the production of levulinic acid from C6 carbohydrate-containing feedstocks will thus generate a complex mixture wherefrom levulinic acid has to be recovered and purified.

The further purification of a biomass hydrolysate to a levulinic acid composition having a higher levulinic acid concentration is described in for example U.S. Pat. Nos. 5,608,105, 4,897,497, 6,054,611, WO2010/030617 and WO2014/087013.

WO2010/030617, for example, describes a purification via filtration, extraction and distillation to a higher concentrated levulinic acid composition. This levulinic acid composition is not of sufficient purity and thus not suitable for many applications mentioned above.

Purification of a biomass hydrolysate to a concentrated levulinic acid composition by the use of only distillation is, for example, mentioned in WO2014/087013. It is known to a person skilled in the art that distillation of levulinic acid always yields small amounts of angelical lactone which is known to cause coloration and low shelf time stability of levulinic acid. This is undesirable which is in particular addressed in U.S. Pat. No. 2,780,588.

Other methods for the purification of a concentrated levulinic acid composition are, for example, mentioned in U.S. Pat. Nos. 2,305,738, 2,029,412, 2,684,982, 2,349,514. These documents hint toward the possibility to purify a concentrated levulinic acid composition via crystallization.

In the mentioned documents it is, however, not specified how crystallization should be performed or what type of crystallization can be used for the purification of levulinic acid.

The purification of a levulinic acid solution to a purity above 99 wt. % is mentioned in U.S. Pat. Nos. 8,507,718 and 9,073,841. These patent publications do not specify the method of crystallization either.

US2014/0316161 mentions crystallization from a dilute (10-50 wt %) levulinic acid composition in a non-specified solvent as a method to obtain pure levulinic acid. The use of diluted levulinic acid is undesirable due to the low temperatures necessary for crystallization of levulinic acid from a diluted levulinic acid. Further, the use of a solvent is undesirable as it brings additional complexity to the purification process.

Crystallization from solution and melt crystallization are, in general, two commonly used processes for the purification of chemical products.

Typical of crystallization from solution is that a solvent is the major compound in a solution that is fed to the crystallization unit. A disadvantage of crystallization from solution is that the impure levulinic acid product needs to be dissolved in solvent, crystallizes in this solvent and, thereafter, recovery of the solvent is required.

Melt crystallization is normally applied for products wherein the crystallizing component is present in a higher amount in the composition than all of the other components together.

Melt crystallization however is considered very unpredictable by the person skilled in the art. This is because the result of melt crystallization does not only depend on the freezing point of the product, the nature of impurities and whether the impurities form an eutectic mixture with the product, but also on the structure of the crystals formed and therefore on their tendency to occlude impurities. Moreover, the size and productivity of the melt crystallization depend on the rate of crystal formation without the occlusion of those impurities. In a review of Wynn (Separate organics by melt Crystallization, Chemical Engineering Progress, March 1992, 52-60) was stated "Unfortunately, in melt crystallization, the critical steps are rate dependent. They cannot be predicted accurately from theory. Laboratory or pilot plant data must be generated before even process feasibility can be established".

The man skilled in the art is led away from the use of crystal seeds for the crystallization of levulinic acid, because in a review article of Jiang et al.; Research progress and model development of crystal layer growth and impurity distribution in layer melt crystallization, IE&C Research, August 2014; it is stated that "commonly industrial configurations of melt crystallization are towers with parallel tubes. Because of this, it is difficult to add and disperse crystal seeds. If seeds added are not distributed evenly along the tower unsatisfactory crystal layer growth may result in tube blocking. The most common method to activate the nucleus is implementing a high super cooling degree on the cold tube surface without seeds."

In this article the wording 'the activation of the nucleus' describes the formation of the first crystals to start the melt crystallization process; this is also called the nucleation.

SUMMARY OF THE INVENTION

The object of the invention is to obtain a levulinic acid that is as pure as possible and preferably has a purity of at least 98 wt. %.

The inventors now surprisingly discovered that levulinic acid with a predetermined purity can be obtained by melt crystallization.

The process according to the invention comprises the following steps:

a. Providing a composition 1, comprising at least 75 wt. % of levulinic acid;
b. Cooling composition 1 to at least one temperature Tc, wherein Tc is a temperature in the range $1.23*(W1)-104.5 \leq Tc$ (° C.) $\leq 1.23*(W1)-89.5$, wherein W1 is the weight % of levulinic acid in composition 1, to obtain a cooled composition 1;
c. Performing melt crystallization of composition 1 comprising the steps of:
  i. Bringing the cooled composition 1 into contact with levulinic acid crystal seeds,
  ii. Allowing the levulinic acid in composition 1 to crystallize at at least one temperature Tc to obtain crystals 1 and liquid 1, and
  iii. Draining of liquid 1;
d. Optionally, treating crystals 1, after draining of liquid 1, by sweating, according to the following steps:
  i. Heating the crystals 1 at a temperature between 5 and 40° C. to obtain crystals 2 and liquid 2, and
  ii. Draining of liquid 2;
e. Melting the crystals 1 or 2, after draining of liquid 1 or 2, to obtain composition 2,
f. Determining the levulinic acid concentration in composition 2 and, in case the levulinic acid concentration is below a predetermined value, repeating steps b, c, optionally d, and e, as many times as necessary to obtain a final composition with a predetermined levulinic acid concentration.

A controlled crystallization of levulinic acid takes place, because of the presence of levulinic acid crystal seeds during crystallization of levulinic acid. This has the advantage that the amount of impurities that are occluded in levulinic acid crystals during crystallization is reduced.

Another advantage is that the final composition will contain only trace amounts of formic acid if any and does not have the smell of formic acid. This is important when the final composition is applied in food or cosmetics.

Another advantage is that the final composition is a clear composition, with a Gardner color below 3, as determined according to ISO 4630.

A further advantage is that the final composition does not contain angelica lactone above 0.1 wt. % ensuring a long shelf life stability.

According to the present invention no strong undercooling needs to be performed to initiate the crystallization of levulinic acid. Composition 1 is not cooled to very low temperatures which is beneficial for the overall energy consumption of the process according to the invention. The use of low temperature cooling media is very costly.

Yet another advantage of the present invention is that crystal growth can take place at a fixed temperature of the cooling medium. It is not required to apply a time dependent temperature profile during the crystal growth stage, which simplifies the operability of the process.

The process according to the invention starts with the provision of a composition 1. Composition 1 comprises at least 75 wt. % of levulinic acid.

Composition 1 can, for example, be obtained by treating a biomass in a sulfuric acid environment such that a biomass hydrolysate containing levulinic acid is obtained. The biomass hydrolysate containing levulinic acid can be subjected to a neutralization step wherein the sulfuric acid, but not the levulinic acid, is neutralized yielding a neutralized biomass hydrolysate. The neutralized biomass hydrolysate is thereafter subjected to a solid liquid separation step to remove insoluble material and to yield a liquid biomass hydrolysate. This liquid biomass hydrolysate can be subjected to an evaporation step to remove water and low boiling compounds from it and to yield an evaporated biomass hydrolysate. The evaporated biomass hydrolysate can be subjected to an additional evaporation step to isolate composition 1 which comprises at least 75 wt. % levulinic acid. The person skilled in the art knows that there are various other methods that are suitable to obtain composition 1.

Composition 1 comprises at least 75 wt. % levulinic acid. Preferably, the amount of levulinic acid in composition 1 is at least 85 wt. %, more preferably at least 90 wt. %, most preferably at least 95 wt. %.

Composition 1 can also contain at most 15 wt. % solvent and at most 10 wt. % impurities, based on the total weight of composition 1.

Preferably, the amount of solvent in composition 1 is at most 10 wt. %, more preferably at most 7 wt. %, most preferably at most 4 wt. %.

Preferably, the amount of impurities in composition 1 is at most 5 wt. %, more preferably at most 3 wt. %, most preferably at most 1 wt. %.

The concentrations of levulinic acid, solvent and impurities in composition 1 are determined with high-performance liquid chromatography (HPLC) and gas chromatography (GC) as described below.

The solvent in composition 1 can be water or an organic solvent. Examples of suitable organic solvents are methyltetrahydrofuran (MTHF), methyl isoamyl ketone, methyl isobutyl ketone, diisobutyl ketone, acetophenone, cyclohexanone, isophorone, neopentyl alcohol, isoamyl alcohol, n-hexanol, n-heptanol, 2-ethyl hexanol, n-octanol, 1-nonanol, 1-undecanol, phenol, 4-methoxyphenol, methylene chloride, methyl isobutyl carbinol, anisol, ethylene glycol di-n-butyl ether, diethyl carbonate, methyl salicylate, methyl levulinate, ethyl levulinate, toluene, methyl-tertiary butyl ether, hexane, cyclohexane, chloro-benzene, dichloroethane, ortho-dichlorobenzene, 2,6-dimethyl cyclohexanone, tetrahydrofuran, furfural and mixtures thereof.

Composition 1 is a liquid composition at room temperature. Because the main component in composition 1 is levulinic acid, composition 1 is also called a melt of levulinic acid.

According to step b composition 1 is cooled. Cooling can for example be performed by bringing composition 1 and the levulinic acid crystal seeds into contact with at least one cooling member. A cooling medium runs through the cooling member to cool the levulinic acid product below a certain temperature. A cooling member can be for example a cooling spiral, a cooling tube, a cooling plate or a cooling jacket. Cooling can be performed by cocurrent and countercurrent circulation through the cooling member.

Cooling is performed by cooling composition 1 to at least one temperature Tc. The temperature Tc is a temperature in the range $1.23*(W1)-104.5 \leq Tc$ (° C.) $\leq 1.23*(W1)-89.5$, wherein W1 is the weight % of levulinic acid in composition 1. The temperature is preferably in the range $1.23*(W1)-100.0 \leq Tc$ (° C.) $\leq 1.23*(W1)-92.5$.

Composition 1 can be cooled in the melt crystallizer or melt crystallizers that will be used in the process according to the invention or composition 1 can be cooled before composition 1 is fed to the melt crystallizer(s).

Melt crystallization is well described in the literature for example in Jansens P. J. and Matsuoka M.: "Melt Crystallization", in: Encyclopedia of Separation Science, Eds. Wilson I. D., Adlard E. R., Cook M., and Poole C. F., Academic Press, San Diego, New York London, Sidney, Tokyo, (2000) 966-975 and in Arkenbout G. F., Melt crystallization technology", Technomic Publishing Company, Inc., Lancaster, Pa. USA, (1995) 239-290.

The purification process according to the invention can be performed in one melt crystallizer or in several melt crystallizers. When more than one melt crystallizers are used the melt crystallizers can be of different types.

One example of a melt crystallization process is layered growth melt crystallization. During layered growth melt crystallization the crystals 1 grow as a layer on a cooled surface. The growth of the crystals 1 is perpendicular to the surface. Industrial equipment for layered growth melt crystallization is normally operated batch-wise, whereby static and dynamic processes can be distinguished. During dynamic melt crystallization there is forced mixing of the melt during crystallization. In static melt crystallization processes the crystal growth occurs from a stagnant melt or a melt that moves only by free convection during the crystallization in the melt crystallizer.

Before melt crystallization a cooled composition 1 is provided. During melt crystallization the following steps are performed:
  i. Bringing the cooled composition 1 into contact with levulinic acid crystal seeds,
  ii. Allowing the levulinic acid in composition 1 to crystallize at at least one temperature Tc to obtain crystals 1 and liquid 1, and
  iii. Draining of liquid 1.

Preferably, the melt crystallization is performed in at least one melt crystallizer.

Preferably, the levulinic acid crystal seeds are added to the surface of composition 1 at the top of the at least one melt crystallizer.

Preferably, the at least one melt crystallizer is a static melt crystallizer.

According to step c.i the cooled composition 1 is brought into contact with levulinic acid crystal seeds. The levulinic acid crystal seeds support the crystallization of the levulinic acid in composition 1.

The levulinic acid crystal seeds preferably are levulinic acid crystal seeds comprising at least 98 wt. % of levulinic acid.

The levulinic acid crystal seeds can be present already inside the melt crystallizer(s) or can be added to the melt crystallizer(s) from an external source. For example, the levulinic acid crystal seeds can be collected in solid form during a previous melt crystallization step. Levulinic acid crystal seeds that originate from several external sources can be combined. Cooled composition 1 can be added first to the crystallizer(s), where after the levulinic acid crystal seeds can be added.

When the levulinic acid crystal seeds are already present inside the melt crystallizer the crystal seeds can be present on the surface of a cooling member or as loose crystal seeds or dispersed crystal seeds in the vessel of the melt crystallizer(s).

The crystal seeds can be provided inside the melt crystallizer by crystallizing a thin film of a levulinic acid composition on the cooling surfaces. For example, a residual composition from a previous crystallization can be partially or completely crystallized as levulinic acid crystal seeds on the cooling surfaces. The film of levulinic acid on the cooling surfaces is partially or completely crystallized by reducing the temperature on the surfaces.

It is also possible to produce a layer of levulinic acid crystal seeds by bringing the cooling surface into contact with a crystal seed-containing suspension of the levulinic acid so as to obtain a layer of levulinic acid crystal seeds by cooling the cooling surface after removal of the suspension. Levulinic acid crystal seeds can also be provided by producing a layer of levulinic acid crystal seeds on a locally restricted, separately cooled cooling surface (cold spot).

Preferably, the amount of levulinic acid crystal seeds present is 0.01-2 wt. %, based on the total weight of composition 1, more preferably 0.05-1.5 wt. %.

When the levulinic acid crystal seeds have been formed outside the melt crystallizer(s) the levulinic acid crystal seeds can be added to the cooled composition 1 in the melt crystallizer(s) as such or as a suspension of levulinic acid crystal seeds. Preferably, the suspension of levulinic acid crystal seeds comprises levulinic acid crystal seeds suspended in liquid levulinic acid. Also, other liquids can be used to suspend the levulinic acid crystal seeds.

After the addition of the levulinic acid crystal seeds or the suspension of levulinic acid crystal seeds, preferably, the levulinic acid crystal seeds are well dispersed in the cooled composition 1.

The number of the levulinic acid crystal seeds is determined by counting the number of seeds in 1 g. of crystals seeds or in 1 g. of slurry of crystal seeds. A microscope or a magnifying glass can be used to support counting. After counting the crystal seeds in 1 g. and the determination of the volume of 1 g. crystal seeds or slurry, the number of crystal seeds in 1000 $cm^3$ is calculated. Preferably, the number of the levulinic acid crystal seeds in the suspension is at least 1 levulinic acid crystal seed per 1000 $cm^3$ of composition 1.

The crystal seeds have a three-dimensional structure. The longest size of a crystal seed is herewith defined as the length of the crystal seed. The length of a crystal seed can be determined by the use of a microscope. The average crystal seed length is determined by the determination of the length of ten crystal seeds and calculating the average crystal seed length. The levulinic acid crystal seeds, preferably have an average crystal seed length of at most 1 cm, more preferably at most 8 mm, most preferably at most 6 mm. The average crystal seed length of the levulinic acid crystal seeds can be very short. Preferably, the average crystal seed length of the levulinic acid crystal seeds is at least 1 μm.

According to step c.ii the levulinic acid that is present in in composition 1 is allowed to crystallize. During crystallization crystals 1 and liquid 1 are formed. Crystallization is performed at at least one temperature Tc. Tc is a temperature in the range as described above. The temperature Tc can be the same temperature as the temperature Tc of the cooled composition 1 or at least one temperature that is higher or lower than the temperature Tc of the cooled composition 1.

The levulinic acid is allowed to crystallize during a certain amount of time. The crystallization can be performed for 5 minutes to 24 hours, preferably for 10 minutes to 20 hours, more preferably for 15 minutes to 10 hours.

Crystallization takes place on the cooled surfaces in the melt crystallizer. During crystallization levulinic acid crystals 1 and liquid 1 are formed. Crystals 1 and liquid 1 are separated by draining liquid 1. When liquid 1 is drained the crystals 1 can still comprise some liquid 1 that adheres to the crystals 1 or is present between the crystals 1. The levulinic acid crystals 1 can be purified by either washing the crystals or subjecting the crystals to sweating as described below.

After the crystals 1 are formed in the melt crystallizer(s) the remaining liquid 1 is drained from the melt crystallizer. The amount of liquid 1 preferably is 30-80 wt. % of composition 1, based on the total weight of composition 1.

After draining of liquid 1 the crystals 1 in the crystallizer can optionally be treated by sweating according to step d.

The treatment of the crystals 1 at an elevated temperature is referred to as sweating. During sweating part of the crystals 1 including impurities are melted and a liquid 2 is formed.

Sweating is performed by heating the crystals 1 at a temperature between 5 and 40° C., preferably at a temperature of 10-35° C.

The temperature determined during sweating is the temperature of the cooling medium. Sweating can be performed at a fixed temperature or at a temperature gradient which is gradually increasing during a certain time period.

Heating can be performed for 5 minutes to 2 hours, preferably for 10 minutes to 1.5 hours, preferably for 15 minutes to 1 hour.

After treatment of the crystals 1 at an elevated temperature the obtained liquid 2 is drained. The liquid 2 will comprise a certain amount of levulinic acid, but also solvent and other impurities. Liquid 2 can be fed to another crystallizer to crystallize (part of) the remaining levulinic acid that is present in liquid 2. The amount of liquid 2 preferably is 5-50 wt. % of composition 1, based on the total weight of composition 1, After separation of liquid 1 or after sweating and draining of the sweating liquid 2 the crystals 1 or 2 are melted to obtain composition 2. Melting is performed by bringing the crystals 1 or 2 to a temperature above the melting temperature of the crystals 1 or 2.

The temperature can be constant or a temperature gradient which is gradually decreasing or increasing during a certain time period. Composition 2 is obtained. Composition 2 comprises a higher weight % of levulinic acid than composition 1.

During melt crystallization levulinic acid is crystallized and melted to obtain composition 2. Composition 2 comprises a higher weight % of levulinic acid than composition 1. Composition 2 is isolated when the concentration of levulinic acid in composition 2 has a predetermined value. A predetermined value is a concentration of levulinic acid in composition 2 that is chosen from a concentration in the range 85-100 wt. %, based on the total weight of composition 2. Preferably, the predetermined levulinic acid concentration in composition 2 is at least 95 wt. %, based on the total weight of composition 2, more preferably at least 98 wt. %, most preferably at least 99 wt. %.

The person skilled in the art determines before the melt crystallization is started which concentration of levulinic acid the final composition should have. This concentration of levulinic acid in the final composition is here and hereafter defined as the predetermined levulinic acid concentration.

When composition 2 does not have the predetermined levulinic acid concentration the melt crystallization can be repeated as many times as necessary to obtain as composition 2 levulinic acid with a predetermined levulinic acid concentration.

The concentration of levulinic acid in composition 2 can, for example, be determined by gas chromatography, by titration or by high-performance liquid chromatography (HPLC) as described further here below.

A levulinic acid concentration is, for example, a levulinic acid concentration of at least 93 wt. %, preferably a concentration of at least 95 wt. %, more preferably a concentration of at least 98 wt. %, in particular a concentration of at least 99 wt. %.

After obtaining composition 2 it is determined if composition 2 can be isolated or if it is necessary to repeat steps b, c, optionally d, and e to obtain the final composition. For repeating the melt crystallization composition 2 is fed to the melt crystallization. The melt crystallization comprises at least one melt crystallizer. When more than one melt crystallizer is present in the melt crystallization the melt crystallizers can be placed in series or parallel. When the melt crystallization is repeated composition 2 can be fed to the same melt crystallizer as composition 1 or to one or more different melt crystallizers.

The steps b, c, optionally d, and e are repeated as many times as necessary to obtain a final composition with a predetermined levulinic acid concentration.

Preferably, the steps b, c, optionally d, and e are repeated 0-6 times, more preferably 1-6 times, most preferably 1-4 times. A person skilled in the art will understand that starting with a levulinic acid composition 1 which has a higher levulinic acid concentration than 75 wt. % will require less repetitions of the melt crystallization to reach a predetermined concentration above 95 wt. % or more preferably 98 wt. %. The use of a low temperature Tc will result in a fast, but less selective crystallization making more repetitions necessary to reach the predetermined concentration above 95 wt. %. The use of a high temperature Tc will result in a slower, but more selective crystallization.

Generally, the number of repetitions depends on the levulinic acid concentration of composition 1, the predetermined concentration and the temperature Tc chosen within the range specified above.

A person skilled in the art will understand that application of sweating will also reduce the number of repetitions that are required to reach a predetermined levulinic acid concentration.

The invention is further directed to a melt crystallizer for the purification of levulinic acid comprising a vessel, at least one cooling member, and means for feeding levulinic acid crystal seeds, wherein the means for feeding levulinic acid crystal seeds comprise a movable pipe for addition of levulinic acid crystal seeds.

The a movable pipe for addition of levulinic acid crystal seeds can comprise one or several openings for the addition of levulinic acid crystal seeds.

The movable pipe for addition of levulinic acid crystal seeds can comprise one or more pipes with a certain length or one or more pipes with several branches. Preferably, the branches contain the openings for the addition of the levulinic acid crystal seeds.

The more openings are provided in the crystal seed addition pipe or the more branches the crystal seed addition pipe has the more evenly the levulinic acid crystal seeds can be distributed over composition 1 that is present in the vessel.

The movable pipe for addition of levulinic acid crystal seeds preferably is located above the surface of composition 1 in the vessel. The pipe for addition of levulinic acid crystal seeds is movable, which means that it can move in different directions above composition 1 in the vessel to guarantee an even distribution of the levulinic acid crystal seeds in composition 1. Preferably, the pipe for addition of levulinic acid crystal seeds moves horizontally above composition 1 in the vessel.

The levulinic acid crystal seeds can be present on the surface of the at least one cooling member or can be added to the vessel. Preferably, the levulinic acid crystal seeds are added to the surface of composition 1 at the top of the vessel. More preferably, the levulinic acid crystal seeds are added in the vicinity of the cooling member or members in the vessel.

DETAILED DESCRIPTION OF THE INVENTION

Figure 1:
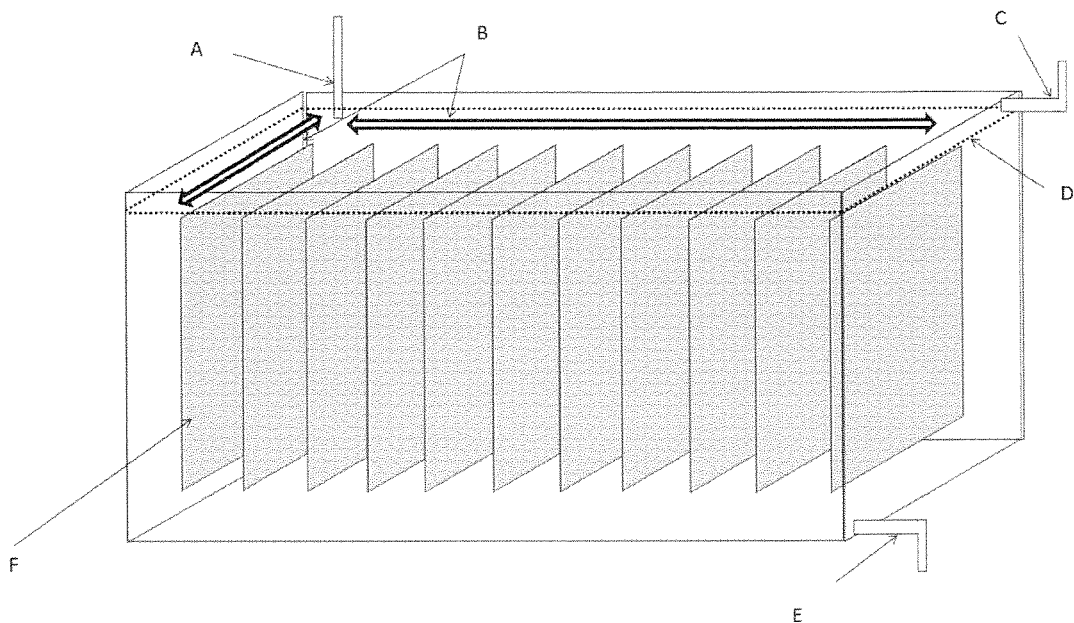
FIG. 1 shows an example of a melt crystallizer.
Figure 2:
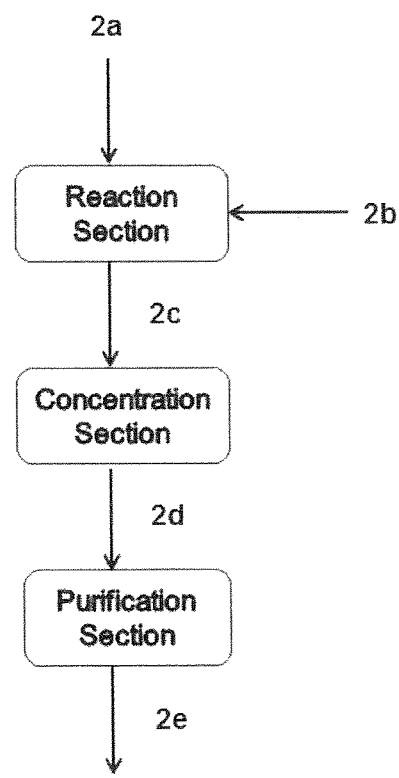
FIG. 2 shows a schematic example of a plant for the production of levulinic acid.

FIG. 1 shows a melt crystallizer comprising various cooling members (F), an inlet for composition 1 (C) and an outlet (E). The melt crystallizer is completely filled with composition 1 and the liquid level of composition 1 is indicated by (D). Composition 1 fills the complete melt crystallizer from the bottom to the top. The top of the melt crystallizer is open.

In FIG. 1 the movable pipe for addition of levulinic acid crystal seeds (A) is shown to be above the liquid level (D) in the melt crystallizer. The movable pipe for addition of levulinic acid crystal seeds (A) can move in horizontally in all directions (B) above the top of the melt crystallizer and can add levulinic acid crystal seeds to the total melt crystallizer because the top of the melt crystallizer is open.

The invention is also directed to a purification section in a plant for the production of levulinic acid comprising at least one melt crystallizer as described above.

The plant comprises a reaction section, wherein biomass (2a) and an acidic catalyst (2b) are introduced in the plant and reacted such that a biomass hydrolysate (2c) containing levulinic acid is obtained.

The biomass hydrolysate (2c) is transferred to a concentration section where the biomass hydrolysate is subjected to recovery and concentration steps such as, for example, filtration, extraction, evaporation, rectification and membrane separation, to yield a levulinic acid composition 1 which comprises at least 75 wt. % levulinic acid. (2d). Levulinic acid composition 1 (2d) is transferred to the purification section wherein at least one melt crystallizer as described above is present to purify composition 1 (2d) to yield levulinic acid with a concentration of at least 95 wt. % (2e).

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention will now be explained by way of the following examples without however being limited thereto.

EXAMPLES

Analysis

Levulinic acid (LA) purity as well as traces of sugars, formic acid and humins were determined via high-performance liquid chromatography (HPLC). Samples were prepared by dilution with water to achieve a final LA concentration between 1 and 5 wt. %. The injection volume was 20 µl. The separation took place on an Agilent HPLC 1260 Infinity equipped with a Shodex KC 811 column and a refractive index detector. The column temperature was 40° C. The eluent (0.05 M Perchloric acid in water) had a flow rate of 1 ml/min. Calibration was carried out using an external standard with results accepted when the calibration curve had a R2 of more than 0.99.

The concentrations of angelica lactone, acetic acid, valeric acid and other volatile compounds were analyzed with gas chromatography (GC) using an Agilent 7820A GC. Carrier gas: Helium, inlet pressure (KPa) 97 kPa, column flow (ml/min) 1 ml/min, total flow 100 ml/min, split ratio 1:100, Injector temperature 270° C., temperature program start 90° C. increase of 20° C./min, hold final temperature of 240° C. 7 min. Total temperature program 13 min. Flame ionization detection was applied for quantitative determination. Calibration was carried out using known compounds in the same range as expected in the samples.

Example 1

49.1 kg of a concentrated levulinic acid composition (83.17 wt. % levulinic acid (LA); 5.36 wt. % formic acid (FA) 5.97 wt. % water and soluble humins to make up for the remaining mass) obtained from acid hydrolysis of corn, was subjected to melt crystallization in a melt crystallizer. The external cooling medium had a fixed temperature of 5° C. during cooling of the feed composition as well as the crystal seed nucleation and growth phase. When the temperature of the concentrated LA composition reached 10° C., 500 grams (about 1 wt. % based on the concentrated LA composition) of levulinic acid crystal seeds (purity 98 wt. % LA, 0.4 wt. % FA, 0.6 wt. % water, average crystal seed length 5 mm, 82 crystal seeds/liter) were added into the melt. Crystallization was allowed for 18 hours. During the crystallization the temperature of the melt was measured and reduced from 12° C. to 10° C. After crystallization liquid 1 was drained from the crystallizer. The crystals were subjected to a sweating step to purify the levulinic acid crystals. Sweating temperature was 25° C. for a period of 3 hours. After sweating and draining of liquid 2, 4.2 kg of levulinic acid crystals was obtained with a purity of 97 wt. % LA, 0.7 wt. % of FA, 2.1 wt. % of water and 1.0 wt. % of soluble humins. The combined liquids 1 and 2 had the following composition: total weight 45.1 kg, 82.0 wt. % LA, 5.8 wt. % FA, 6.3 wt. % water and soluble humins to make up for the remaining mass.

Example 2

25.02 kg of a concentrated levulinic acid composition (84.4 wt. % LA; 5.1 wt. % FA 6.82 wt. % water and soluble humins to make up for the remaining mass), obtained from acid hydrolysis of corn, was subjected to melt crystallization cycle in a melt crystallizer. The external cooling medium had a fixed temperature of 5° C. during cooling of the feed composition and crystallization. When the temperature of the concentrated LA composition reached 10° C., 25 grams of levulinic acid crystal seeds (purity 98 wt. % LA, 0.4 wt. % FA, 0.6 wt. % water, average crystal seed length 5 mm, number of crystal seeds: 8 particles/liter) were added into the levulinic acid composition. Crystallization was allowed for 18 hours. During crystallization the temperature of the levulinic acid composition was measured and varied between 11 and 12° C. After crystallization liquid 1 was drained from the crystallizer. The crystals were subjected to a sweating step to purify the levulinic acid crystals. Sweating temperature was 25° C. for a period of 3 hours. After sweating and draining of liquid 2, 2.1 kg of levulinic acid crystals was obtained with a purity of 98.2 wt. % LA, 0.1 wt. % of FA, 0.67 wt. % of water and soluble humins to make up for the remaining mass. The combined liquids 1 and 2 had the following composition: total weight 22.6 kg, 83.1 wt. % LA, 5.52 wt. % FA, 7.43 wt. % water and soluble humins to make up for the remaining mass.

Example 3

24.12 kg of a concentrated levulinic acid composition (83.9 wt. % LA; 4.54 wt. % FA 7.24 wt. % water and soluble humins to make up for the remaining mass), obtained from acid hydrolysis of corn, was subjected to melt crystallization in a melt crystallizer. The external cooling medium had a fixed temperature of 5° C. during cooling of the feed composition and crystallization. When the temperature of the concentrated LA composition reached 10° C., 500 g of a suspension of levulinic acid crystal seeds at temperature 12° C., containing 5 wt. % crystal seeds (mother liquid 83.9 wt. % LA, crystal seed purity 98 wt. % LA, 0.4 wt. % FA, 0.6 wt. % water, average crystal seed length 5 mm, number of crystal seeds: 8 crystal seeds/liter) was added into the levulinic acid composition. Crystallization was allowed for 18 hours. During crystallization, the temperature of the levulinic acid composition was measured and reduced from 13° C. to 11° C. After crystallization, liquid 1 was drained from the crystallizer. The crystals were subjected to a sweating step to purify the levulinic acid crystals. Sweating temperature was 25° C. for a period of 3 hours. After sweating and draining liquid 2, 2.07 kg of levulinic acid crystals was obtained with a purity of 97.6 wt. % LA, 0.73 wt. % of FA, 1.41 wt. % of water and soluble humins to make up for the remaining mass. The combined liquid 1 and 2 had the following composition: total weight 22.2 kg, 82.5 wt. % LA, 4.92 wt. % FA, 7.56 wt. % water and soluble humins to make up for the remaining mass.

Example 4

93.1 grams of a liquid obtained by melting the crystals, obtained during crystallization example 3 (97.6 wt. % LA, 0.73 wt. % of FA, 1.41 wt. % of water and soluble humins to make up for the remaining mass), was subjected to a second melt crystallization. The external cooling medium had a fixed temperature of 20° C. during cooling of the feed composition and crystallization. When the temperature of the feed composition reached 22° C., 1.2 g of levulinic acid crystal seeds (purity 98 wt. % LA, 0.4 wt. % FA, 0.6 wt. % water, average crystal seed length 5 mm, 7 crystal seeds/liter) were added into the levulinic acid composition. Crystallization was allowed for 4 hours. During crystallization the temperature of the levulinic acid composition was measured and was relatively constant at 24° C. After crystallization and draining of liquid 1 the crystals were subjected to a sweating step to purify the levulinic acid crystals. Sweating temperature was 30° C. for a period of 2 hours. After sweating and draining of liquid 2, 23.0 g of levulinic acid crystals was obtained with a purity of 99.3 wt. % LA, 0.10 wt. % of FA, 0.6 wt. % of water and soluble humins to make up for the remaining mass. The combined liquid 1 and 2 accounted for 69.4 g with a composition of 97.1 wt. % LA, 0.95 wt. % FA, 1.71 wt. % water and soluble humins to make up for the remaining mass.

Comparative Experiments

Experiment A 200.1 grams of a liquid obtained by melting the crystals, obtained during crystallization example 3 (97.6 wt. % LA, 0.73 wt. % of FA, 1.41 wt. % of water and soluble humins to make up for the remaining mass), were subjected to a second melt crystallization. The external cooling medium had a fixed temperature of 10° C. during cooling of the feed composition and crystallization. No levulinic acid crystal seeds were added to the levulinic acid composition. The temperature of the liquid reached 11° C. After 5 hours crystallization time the first levulinic acid crystals were observed at the surface of the stainless-steel U-tube. In 25 minutes the complete levulinic acid composition was solidified, implying no purification effect by selective LA crystallization.

Experiment B 4.3 kg of a concentrated levulinic acid composition (83.9 wt. % LA; 4.54 wt. % FA 7.24 wt. % water and soluble humins to make up for the remaining mass), obtained from acid hydrolysis of corn, was subjected to a melt crystallization. The temperature of the external cooling medium was stepwise reduced with 1° C. per hour from 5° C. till-20° C. during 24 hours. No levulinic acid crystal seeds were added to the levulinic acid composition. Even after 5 hours crystallization time at −20° C. no crystals were formed.

Experiment C 4.1 kg of a concentrated levulinic acid composition (83.9 wt. % LA; 4.54 wt. % FA 7.24 wt. % water and soluble humins to make up for the remaining mass), obtained from acid hydrolysis of corn, was subjected to melt crystallization in a melt crystallizer. The temperature of the external cooling medium was also stepwise reduced with 1° C. per hour starting from 5° C. After 8 hours crystallization time, at a cooling medium temperature of minus 3° C. the first levulinic acid crystals were observed in the crystallizer. The LA crystals were allowed to grow for 1 hour. Dendritic crystal growth was observed, indicating fast growth. After crystallization 3.7 kg of concentrated levulinic acid composition was drained from the crystallizer (82.7 wt. % LA, 7.37 wt. % FA, 8.43 wt. % water and soluble humins to make up for the remaining mass). The crystals were subjected to a sweating step to purify the levulinic acid crystals. Sweating temperature was 25° C. for a period of 3 hours. After sweating, 0.27 kg of levulinic acid crystals was obtained with a purity of 92.7 wt. % LA, 2.31 wt. % of FA, 3.52 wt. % of water and soluble humins to make up for the remaining mass.

Experiments B and C show that without adding levulinic acid crystal seeds the purification process is not controllable and when crystals were formed the crystals were of poor quality.

What is claimed is:
1. A process for the purification of levulinic acid, comprising the following steps:
   a. providing a composition 1, comprising at least 75 wt. % of levulinic acid;
   b. cooling composition 1 to at least one temperature Tc, wherein Tc is a temperature in the range 1.23*(W1)–

$104.5 \leq Tc\ (°\ C.) \leq 1.23*(W1)-89.5$, wherein W1 is the weight % of levulinic acid in composition 1, to obtain a cooled composition 1;

c. performing melt crystallization of composition 1 comprising the steps of:
  i. bringing the cooled composition 1 into contact with levulinic acid crystal seeds,
  ii. allowing the levulinic acid in composition 1 to crystallize at at least one temperature Tc to obtain crystals 1 and liquid 1, and
  iii. draining of liquid 1;

d. optionally, treating crystals 1, after draining of liquid 1, by sweating, according to the following steps:
  i. heating the crystals 1 at a temperature between 5 and 40° C. to obtain crystals 2 and liquid 2, and
  ii. draining of liquid 2;

e. melting the crystals 1 or 2, after draining of liquid 1 or 2, to obtain composition 2, f. determining the levulinic acid concentration in composition 2 and, in case the levulinic acid concentration is below a predetermined value, repeating steps b, c, optionally d, and e, as many times as necessary to obtain a final composition with a predetermined levulinic acid concentration.

2. The process according to claim 1, wherein the amount of levulinic acid crystal seeds is 0.01-2 wt. %, based on the total weight of composition 1.

3. The process according to claim 1, wherein the levulinic acid crystal seeds are added as such to cooled composition 1.

4. The process according to claim 1, wherein the levulinic acid crystal seeds are added to cooled composition 1 as a suspension of the levulinic acid crystal seeds in liquid levulinic acid.

5. The process according to claim 4, wherein the number of the levulinic acid crystal seeds in the suspension is at least 1 crystal seed per 1000 $cm^3$ of composition 1.

6. The process according to claim 1, wherein the levulinic acid crystal seeds have an average crystal seed length of at most 1 cm.

7. The process according to claim 1, wherein the melt crystallization is performed in at least one melt crystallizer.

8. The process according to claim 7, wherein the levulinic acid crystal seeds are added to the surface of composition 1 at the top of the at least one melt crystallizer.

9. The process according to claim 7, wherein the at least one melt crystallizer is a static melt crystallizer.

10. The process according to claim 1, wherein the predetermined levulinic acid concentration in composition 2 is at least 98 wt. %, based on the total weight of composition 2.

11. The process according to claim 1, wherein steps b, c, optionally d, and e are repeated 0-6 times.

12. The process according to claim 1, wherein the crystallization in step c.ii is performed for 5 minutes to 24 hours.

13. The process according to claim 1, wherein the heating in step d.i is performed for 5 minutes to 2 hours.

14. The process according to claim 2, wherein the levulinic acid crystal seeds are added as such to cooled composition 1, wherein the levulinic acid crystal seeds are added to cooled composition 1 as a suspension of the levulinic acid crystal seeds in liquid levulinic acid.

15. The process according to claim 14, wherein the number of the levulinic acid crystal seeds in the suspension is at least 1 crystal seed per 1000 $cm^3$ of composition 1, and wherein the levulinic acid crystal seeds have an average crystal seed length of at most 1 cm.

16. The process according to claim 15, wherein the melt crystallization is performed in at least one melt crystallizer, and wherein the levulinic acid crystal seeds are added to the surface of composition 1 at the top of the at least one melt crystallizer.

17. The process according to claim 16, wherein the at least one melt crystallizer is a static melt crystallizer, and wherein the predetermined levulinic acid concentration in composition 2 is at least 98 wt. %, based on the total weight of composition 2.

18. The process according to claim 17, wherein steps b, c, optionally d, and e are repeated 0-6 times, wherein the crystallization in step c.ii is performed for 5 minutes to 24 hours, and wherein the heating in step d.i is performed for 5 minutes to 2 hours.

* * * * *